United States Patent [19]

Prine

[11] Patent Number: 4,535,629
[45] Date of Patent: Aug. 20, 1985

[54] METHOD AND APPARATUS FOR STRUCTURAL MONITORING WITH ACOUSTIC EMISSION AND USING PATTERN RECOGNITION

[75] Inventor: David W. Prine, Maywood, Ill.

[73] Assignee: Chamberlain Manufacturing Corporation, Elmhurst, Ill.

[21] Appl. No.: 590,378

[22] Filed: Mar. 16, 1984

[51] Int. Cl.³ ............................................. G01N 29/04
[52] U.S. Cl. ........................................ 73/587; 364/508
[58] Field of Search ................ 73/587, 801, 658, 659; 364/508; 340/683

[56] References Cited

U.S. PATENT DOCUMENTS

| | | | |
|---|---|---|---|
| 3,379,972 | 4/1968 | Foster et al. | 73/1 DV |
| 3,455,149 | 7/1969 | Foster et al. | 73/658 |
| 3,503,251 | 3/1970 | Flagge | 73/658 |
| 3,782,183 | 1/1974 | O'Connor et al. | 73/587 |
| 3,858,439 | 1/1975 | Nakamura | 73/587 |
| 3,936,822 | 2/1976 | Hirschberg | 73/658 |
| 3,985,024 | 10/1976 | Horak | 73/587 |
| 4,009,463 | 2/1977 | Vercellotti et al. | 73/587 |
| 4,010,637 | 3/1977 | Harwell et al. | 73/658 |
| 4,036,057 | 7/1977 | Morais | 73/587 |
| 4,086,816 | 5/1978 | Jon et al. | 73/587 |
| 4,086,817 | 5/1978 | Jon et al. | 73/587 |
| 4,207,771 | 6/1980 | Carlos et al. | 73/587 |
| 4,413,507 | 11/1983 | Drew et al. | 73/659 |

*Primary Examiner*—Stephen A. Kreitman
*Attorney, Agent, or Firm*—Hill, Van Santen, Steadman & Simpson

[57] ABSTRACT

An acoustic emission monitoring system used for monitoring fatigue crack growth in metal or other materials such as occur, for example, in highway bridges during normal traffic loading. The transducers are placed on the plates to be tested to allow detection of acoustic emission from a particular site. By applying specific recognition methods to the acoustic emission AE, detection of flaws can be detected from a random noise background. The pattern recognition technique first subjects the received AE energy to an energy window test and if the energy is within the window, it is subjected to a rate test and if the energy exceeds predetermined rates, it is passed to a location test so as to locate the position of flaws.

7 Claims, 13 Drawing Figures

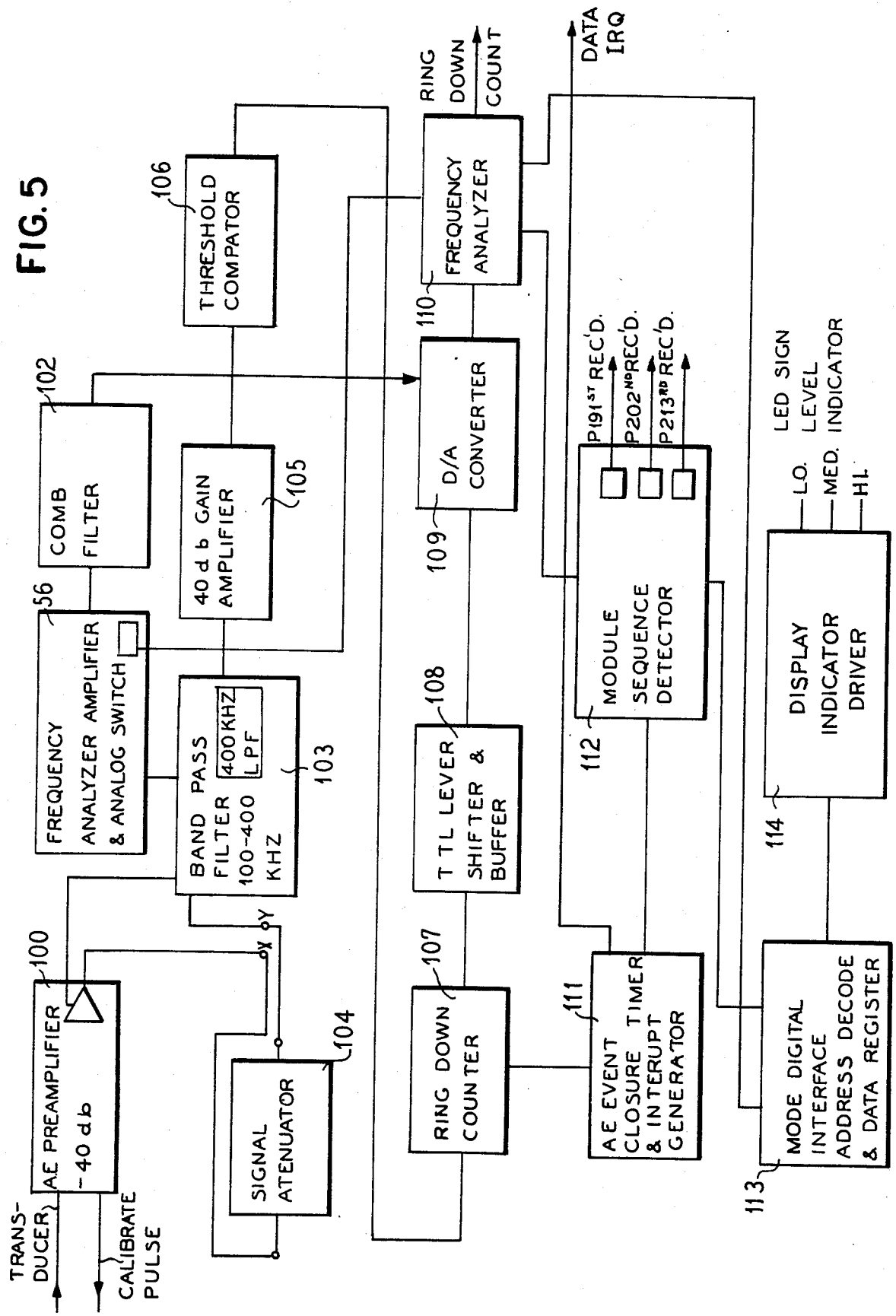

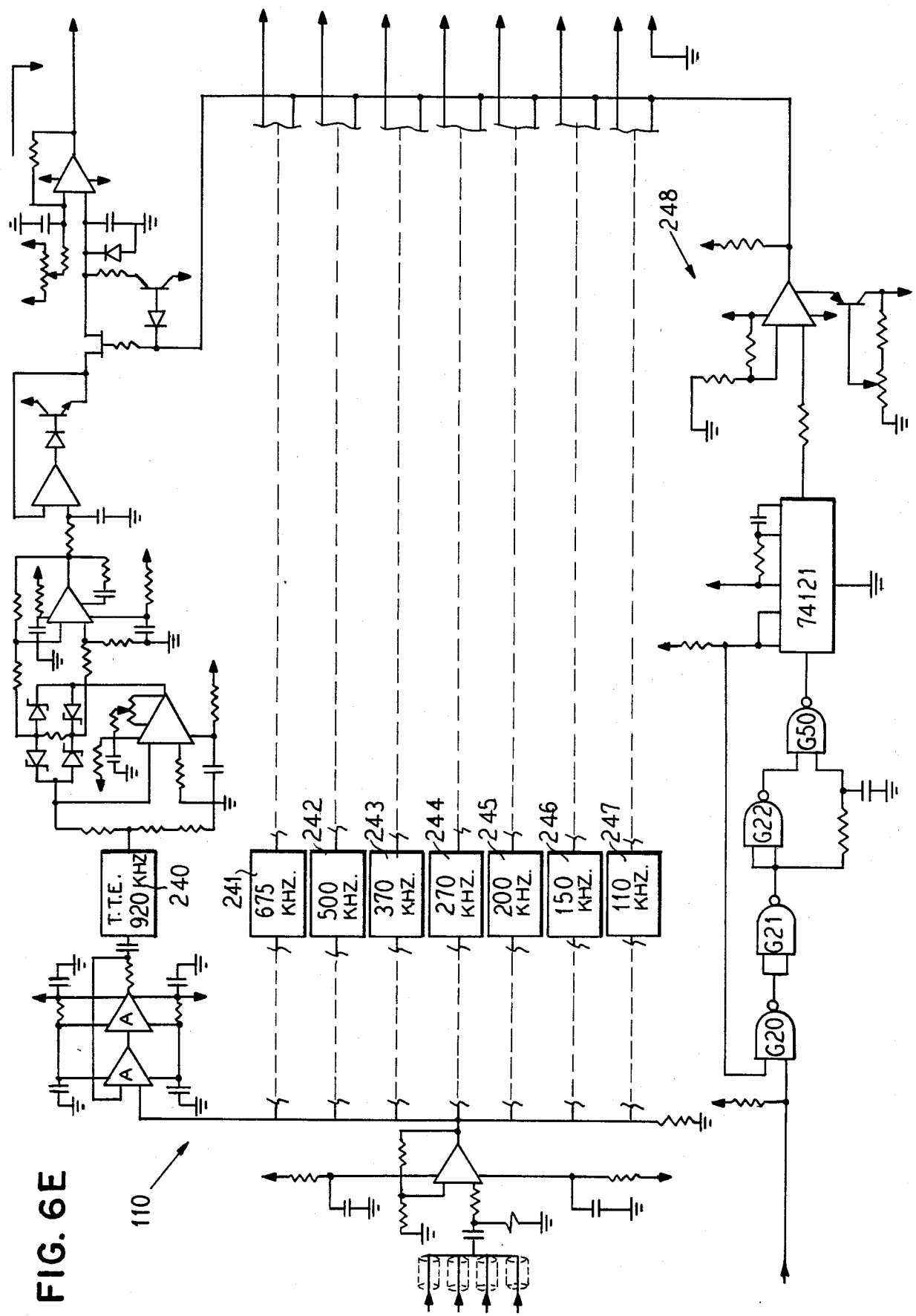

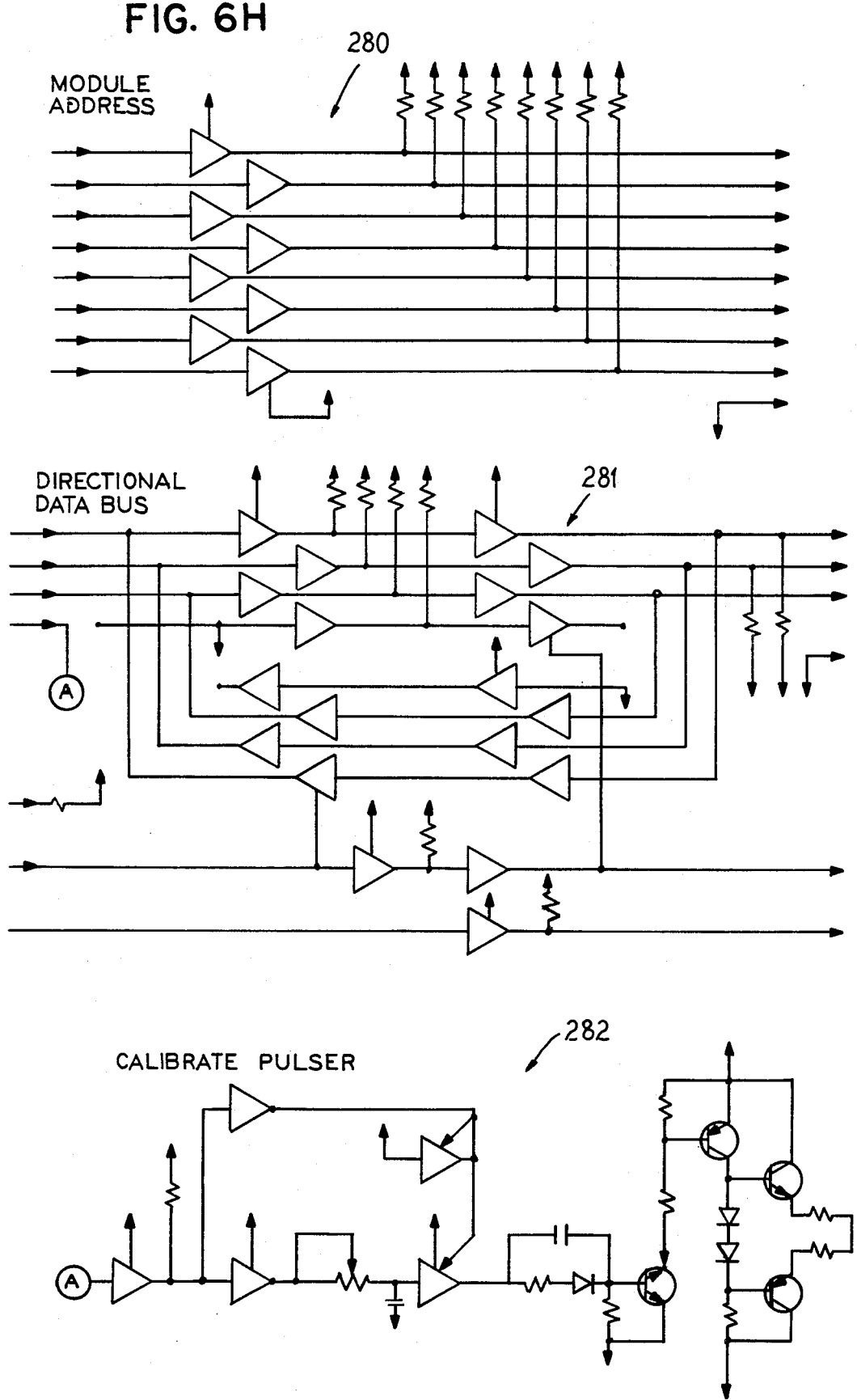

METHOD AND APPARATUS FOR STRUCTURAL MONITORING WITH ACOUSTIC EMISSION AND USING PATTERN RECOGNITION

BACKGROUND OF THE INVENTION

1. Field of the Invention

This invention relates in general to detectors for acoustic emission and in particular to a novel method and apparatus for testing with acoustic emission test samples such as highway bridges.

2. Description of the Prior Art

U.S. Pat. No. 4,024,522 assigned to the assignee of the present inventon which issued on May 17, 1977 entitled "Acoustic Emission System For Welding Flaw Detection" discloses a flaw detection system for use during a continuous welding process wherein a transducer provides a signal burst for each acoustic emission burst from an article being welded and the acoustic emission is filtered so as to pass frequencies between about 100 and 550 KHz. Signal bursts which pass through the filter are then subjected to an amplitude discrimination and then to a rate detection and if the detected rate is high enough then an alarm is given to indicate that a flaw occurs in the welded material.

SUMMARY OF THE INVENTION

There has been a developing need to detect cracks and other flaws in materials such as bridges used by vehicles and older bridges are being subject to loadings in excess of their original design capacity. Due to the combined effects of age, atmosphere and loading the structures are prone to sub-critical growing cracks. Newer bridges employ "fracture-critical" structural members. Such bridges rely on high strength steels and welding fabrication processes to provide economical structures. Such bridges have demonstrated susceptibility to crack problems caused by fabrication related defects.

The present invention relates to a non-destructive evaluation technique wherein acoustic emission AE is monitored from bridges and the output is correlated so as to determine the integrity of the structural members of the bridge. The environment for use of AE techniques result in many problems due to the environment, the complexity and size of the bridges. The uncertainty of internal defect excitation also results in a further limitation on the AE technique. However, the main limitation using prior art acoustic emission technology is the ability to relate AE signals to the source of specific events and, thus, identify the location of faults.

The prior art acoustic emission apparatus such as disclosed in U.S. Pat. No. 4,024,522 can perform standard signal analysis using the signal in digital form. However, this prior art equipment and methods do not allow the location and form of the faults to be identified.

The present invention comprises a micro-processor-based acoustic emission monitoring system that can detect locate and characterize flaws in bridges or other structures. In the present invention, at least two, AE sensors are used and these sensors are attached to the bridge plates, as for example, utilizing permanent magnets which hold them to the bridge. In a particular example, the sensors were mounted 64 inches apart along the edge of an angle splice plate. They were acoustically coupled to a cross-beam and the upper flange (which was the site of a crack) was located about 16 inches down from the top AE sensor which comprises the channel 1 sensor. A third sensor was attached as near as possible to the site of the crack and the third sensor was driven by a high power pulser and was periodically pulsed so as to produce a simulated AE burst which could be picked up by the other two sensors so as to provide check-out of the AE system performance.

The method consists of subjecting each AE event to a series of tests performed in sequence. The present invention comprises a flaw detection model which uses a three step process. Initially computed with a ring down count for each event, the received energy lies within preset limits, the event is passed to a next test which comprises a rate test. The rate test requires that there be some number N of events that have passed the ring count down energy test within some preset time interval. The final test is a test to see if all of the events that pass the previous two tests originate from the same location or at least within some preset locational tolerances. The combination of the rate and location tests provide a very high discrimination against interfering background acoustical signals because a growing flaw or crack will produce higher rates of AE burst emission than other processes and the flaw being a localized phenomena will produce a high rate from a specific well defined location. The present invention using a source location as a flaw detection criteria differs radically from prior art traditional use of source location information. In prior art AE monitoring equipment, source location may be used to lock out given areas or regions of the structure under tests, in other words, the system may be made to listen only to a specific location. This approach requires prior knowledge of the probable location of a flaw and its degree of success depends on the flaws being locationally isolatable from potentially interfering sources and such condition, for example, is seldom met in a typical vehicle bridge structure. In the present invention any source location lying between the transducers is monitored and when a group of AE events has satisfied the ring down count and event rate tests then a test is made to see that all the group events lies within a preset locational limit of each other. For example, if a one inch tolerance is used, then the events that satisfy the first two tests must have the same order of receipt at transducers 1 and 2 and their locational clock indications must not differ by more than 16 micro seconds. If this criteria is met, than a flaw indication is indicated at the appropriate location.

Also, the present invention in addition to the detection of the flaw related AE, applies an adaptive frequency analysis model to the flaw related events and provides a two category classification of the source, crack, or non-crack.

In actual use of equipment according to the invention, five sites were monitored over a three day period. One of the sites which produced AE indications, were repeated on two consecutive days and were properly located in known crack regions.

Thus, the present invention provides a new and novel method of locating faults in metal plates such as bridge structures utilizing acoustic emission energy.

Other objects, features and advantages of the invention will become readily apparent from the following description and claims when read in view of the drawings in which:

BRIEF DESCRIPTION OF THE DRAWINGS

FIG. 5 is a block diagram illustrating the invention; and

FIGS. 6A through 6H comprise electrical schematics of the invention.

DESCRIPTION OF THE PREFERRED EMBODIMENTS

Figure 1:
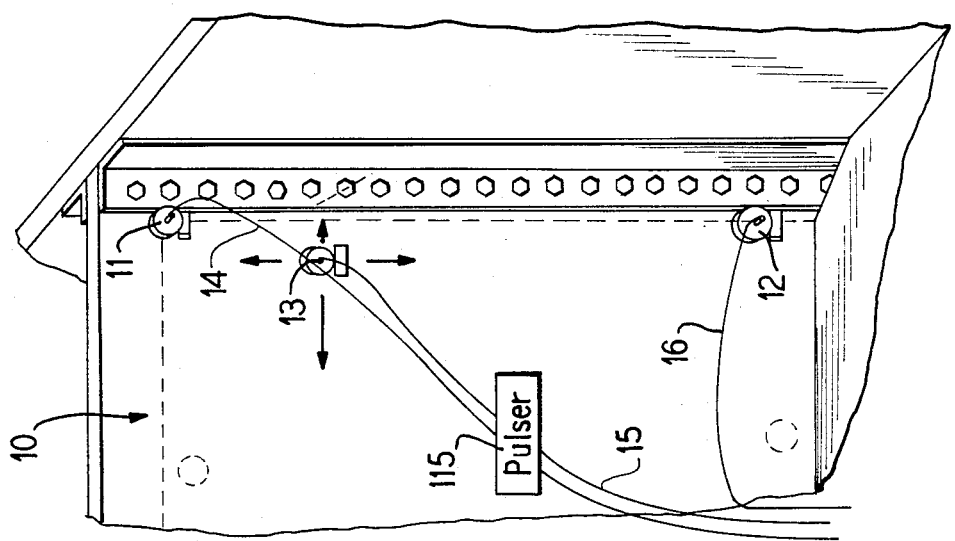
FIG. 1 illustrates a section of a test specimen with three transducers of the invention mounted thereon.

The present invention allows detection of flaws as, for example, in bridges to be determined. For example, FIG. 1 illustrates a bridge 10 to which a standard resonant acoustic emission sensor 11 is attached at a first location. The sensor 11 incorporates a magnet for holding it against the metal plate of the bridge. A second sensor 12 is attached to the bridge 10 at a location about 64 inches below the first sensor 11. A third sensor 13 was attached to the bridge 10 at a point between the sensors 11 and 12 and about 16 inches below the sensor 11. The sensor 13 was driven by a pulser 115 which periodically applies pulses to it. For testing the system, leads 14, 15 and 16 are respectively connected to the sensors 11, 12 and 13.

Figure 2:
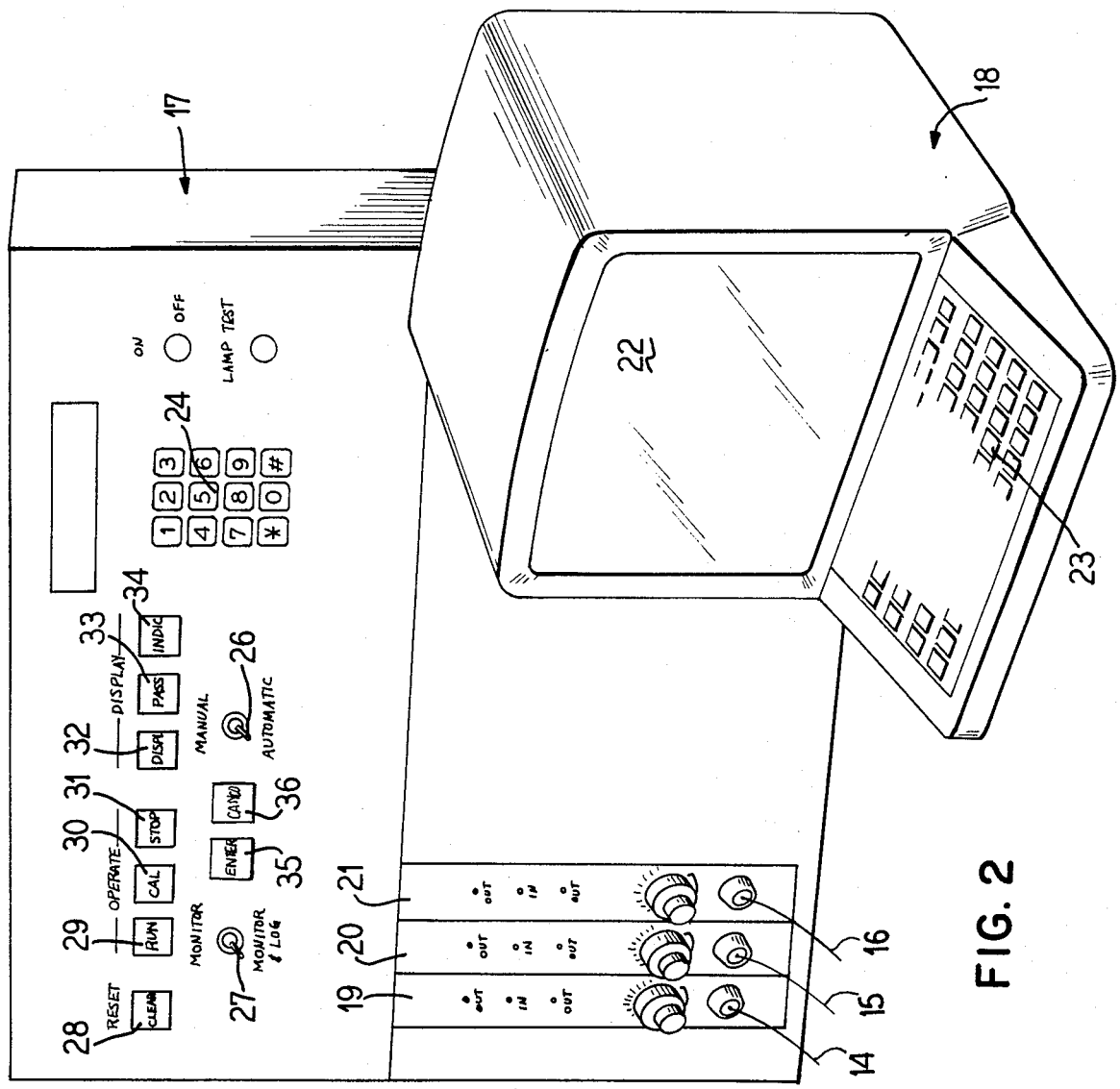
FIG. 2 is a view of the console and the monitor of the invention.

FIG. 2 illustrates a monitor 18 and a control panel 17. The monitor 18 has a keyboard 23 and a display panel 22. The control panel 17 has three analog units 19, 20 and 21 which are respectively connected by leads 14, 15 and 16 to the sensors 11, 12 and 13. Each of the analog units has concentric gain switches as well as three LED indicators which indicate overflow, underflow and a ring down count between a predetermined amount as, for example, between 100 and 1000, for example. The reset switch 28 is provided on the control unit 17 as are run 29, calibrate 30, and stop 31 switches. Display switches 32, 33 and 34 are provided as is a monitor and log switch 27, an enter switch 35, a cancel switch 36 and a manual-automatic switch 26. Numeric push buttons 24 are provided on the control unit 17.

Figure 3:
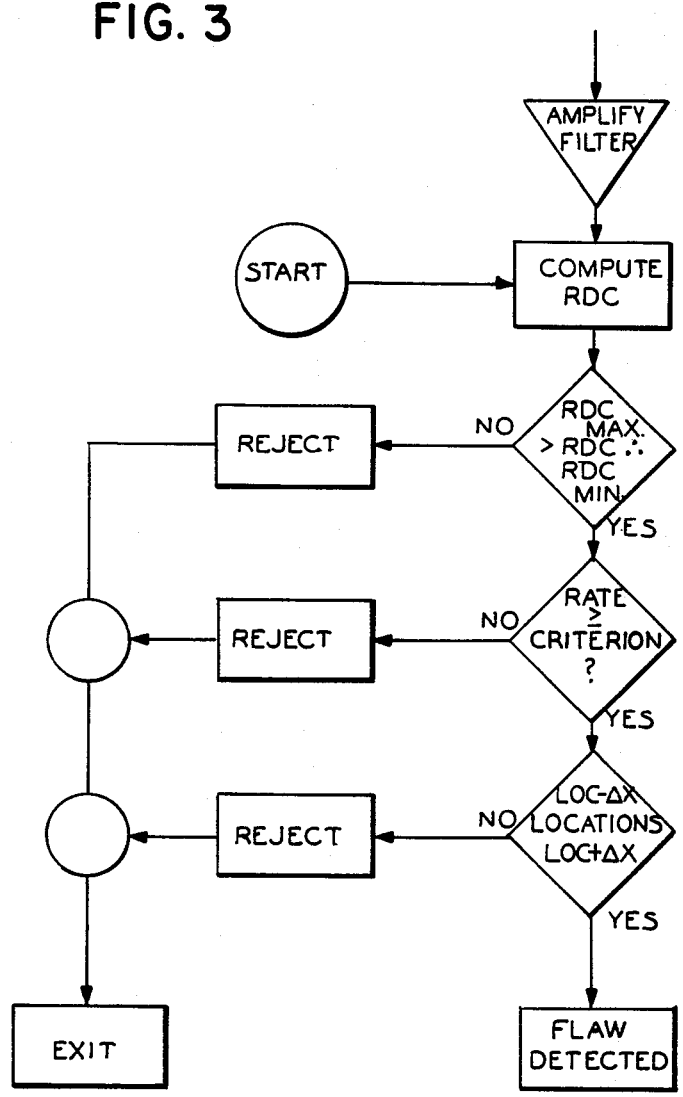
FIG. 3 is a flow diagram illustrating the invention.

The invention performs the required pattern recognition for flaw detection in real time. The process consists of subjecting each of the acoustic emission events to a series of tests performed in sequence. A three step process is utilized. FIG. 3 illustrates a flow chart of the process. First, the ring down count RDC for each event is made and then the first test is applied. If the ring down count lies within preset limits, the event is passed on to the next test which is a rate test. The rate test requires that there be some number N of events (that have also passed the RDC test) within some preset time interval. If the events pass the rate test, they are then passed to a final location test which determines if all of the events which pass the previous two tests originate from the same location or at least within some preset location tolerance. The combination of the rate and location tests provides very high discrimination against interfering background acoustic signals and the assumption being that a growing flaw will produce higher rates of AE burst emission than other processes and that the flaw being a localized phenomena will produce the high rate from a specific well defined location. The use of source location as a flaw detection criteria differs radically from prior art traditional use of source location information. In conventional AE monitoring equipment, source location may be used to lock out given areas or regions of the structure under test, in other words, the system may be made to listen only to the specific location. This approach requires prior knowledge of the probable location of a flaw and the degree of success depends on the flaws being locationally isolatable from potentially interfering sources, a condition that is seldom met in typical bridge structures, for example. The present invention does not limit the monitor to a specific location. Any source location lying between the transducers is monitored. When a group of acoustic emission events has satisfied the first two criteria which are the ring down count test and the event test, a test is made to see that all of the groups of events lie within preset locational limits of each other. For example, if a one inch tolerance is used, then the event that satisfied the first two tests must have the same order of receipt at transducers 1 and 2 and their locational clock indications must not differ by more than 16 counts. If this criteria is met than a flaw indication will be recognized at the appropriate location.

The present invention in addition to detecting flaws applies an adaptive frequency analysis model to the flaw related event and provides a two category classification of the source crack or non-crack.

The invention was used to monitor several sites on a bridge where known fatigue cracks exist. The two channel linear location system suppress the acoustic noise from fastener fretting and reliably and clearly detected crack related activity even though the cracks were either immediately adjacent to or coincidence with bolt holes.

It was proved that flaw growth related activity can be detected from noisy structural details and this work also showed that very small amounts of fatigue crack growth can be detected when a bridge is subjected to routine loadings. The volume of traffic on the bridges under test was not significant compared to bridges in more urban locations. Nor was the magnitude of the bridge loadings unusual. All the valid AE activity was usually correlated with one or two heavily loaded semi-trailer trucks; this type of traffic was very infrequent. Yet it took no more than $2\frac{1}{2}$ hours to excite the expected AE activity at the flaw sites.

The invention indicates that unusual load procedures such as heavy proofing loads are not necessary to excite AE activity from a crack which is already experiencing sub-critical growth due to service loading. In service, AE monitoring of a test area for a period of less than 4 hours was sufficient to detect fatigue cracks on steel bridges subjected to normal structural loading patterns. Structural discontinuities which are harmless do not generate any AE activity and can be ignored.

Figure 4:
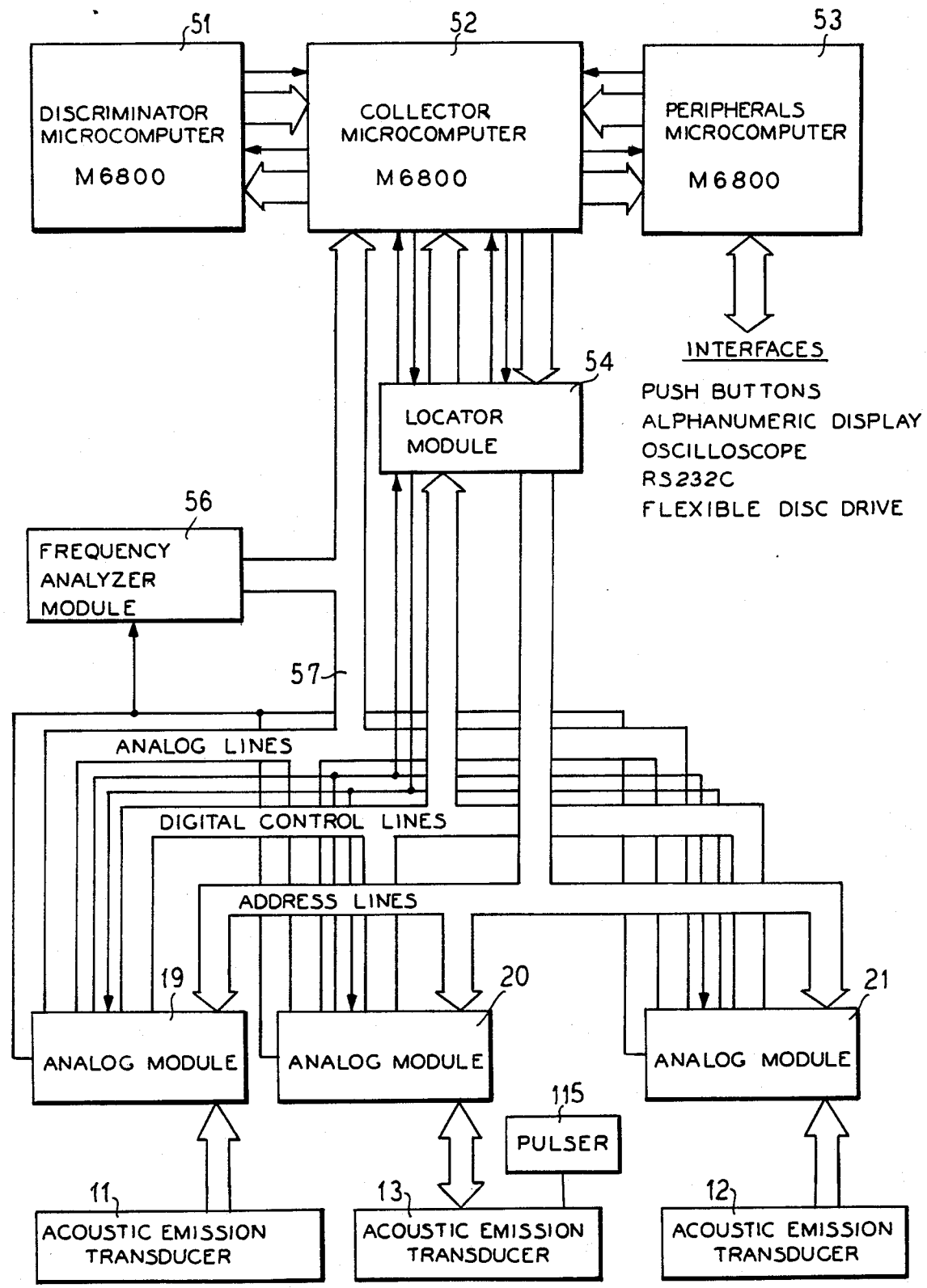
FIG. 4 is a block diagram illustrating the invention.

FIGS. 4 through 6 illustrate the equipment schematics and block diagrams of the equipment of the invention.

FIG. 4 illustrates a functional block diagram of the invention which utilizes both analog and digital computer operations. The analog section pre-processes the acoustic emission signals into ring down counts, frequency activity and location data. The computer section distributes and processes the data into indication types intensities and locations.

The computer section is composed of three microcomputers 51, 52 and 53 which might, for example, be of type Motorola M6800 microprocessors. The microcomputer 52 interfaces with the analog bus 57 which is connected to the analog modules 19, 20 and 21 and it collects data on an interruptable asynchronous basis such as acoustic emission data from the analog bus 57. It then sends such data to the discriminator microcomputer 51 and to the peripheral microcomputer 53. The discriminator microcomputer 51 processes the data to determine if an abnormality indication has occurred and, if so, classifies the indication as to type and relative intensity. After an indication has been processed, the discriminator microcomputer 51 passes the information to the collector microcomputer 52 which transfers the indication to the peripheral microcomputer 53 which supplies it to the monitor 22. The peripheral microcomputer 53 interfaces with all of the peripherals used to control the apparatus and to store and display the results of the monitoring. The basic peripherals are the front panel push buttons 24, the key pad 23, the various state switches 28 through 36 and the alphanumeric display 22.

In a particular example when an acoustic emission signal is received by one of the analog modules 19, 20 and 21, the signals are amplified by 40 dB and then attenuated by a resistive network controlled by the front panel gain selectors. The signal is then high pass filtered at 100 kHz and split into two branches. One branch amplifies the signal 20 dB and sends it along the analog bus to the frequency analyzer module 56. The other branch low pass filters the signal at 400 kHz and amplifies it 40 dB and compares it with a one volt threshold and uses it to drive a counter which computes the ring down count. The first pulse out of the comparator is used to start clocks in the locator module 54. A short time after passage of the last pulse of the train out of the comparator, usually 7-20 milliseconds, the analog module logic decides that the acoustic event is over and initiates an interrupt to the "collector microcomputer 52". During this post event time out, other transducers such as 12 and 13 have also been detecting other parts of the same wave front and their associated analog modules have processed the received signals in a similar manner. The collector microcomputer 52 interrogates the analog modules 19, 20 and 21 to find the time order of acoustic emission reception. It does this by sequencing through all of the module addresses using the address lines on the analog bus and strobing each module to obtain the right time order bit pattern which is passed to the collector data port. The collector microcomputer 52 loads the address of each responding module and its reception time order into a time order look up table and then uses this table to interrogate the responding modules for the respective ring down count values in the order of their reception. If at least one ring down count exceeds a set threshold, as for example, 12 in a particular example, the collector microcomputer 52 proceeds to acquire the eight frequency activities and the two location clocks. It then resets all modules on the analog bus and interrupts both the discriminator microcomputer 51 and the peripheral microcomputer 53 and transfers this data package along with the clock time to them. If no ring down count exceeds the set threshold, the acoustic emission is ignored and the modules on the analog bus are reset.

When acoustic emission data transfers from the collector microcomputer 52 out to the discriminator microcomputer 51 and to the peripheral microcomputer 53, the intercomputer interfaces effect a high speed handshake—secured transfer.

FIG. 5 is a block diagram illustrating the processing of the information from the analog modules 19, 20 and 21 and the acoustic emission transducers 11, 12 and 13. An acoustic emission pre-amplifier 100 receives an output from a transducer 11, 12 or 13. It is to be realized that there is a separate channel for each transducer and supplies an output to a band pass filter 103 through the signal attenuator 104. The band pass filter 103 supplies an output to the frequency analyzer amplifier 56 which supplies an output to a comb filter 102. The comb filter supplies an input to a digital to analog converter 109 which also receives an input from a level shifter and buffer 108. The ring down counter 107 supplies an input to the level shifter and buffer 108 and receives an input from the threshold comparator 106 which receives an output from a 40 dB gain amplifier 105. The amplifier 105 receives an output from the band pass filter 103 through the 400 kHz low pass filter incorporated into the band pass filter 103. The ring down counter supplies an output to the AE event closure timer and interrupt generator 111 which supplies an output to the module sequencer 112 which also receives input from the other transducers. The ring down counter 107 also supplies an output to the level shifter and buffer 108 which supplies an output to the digital to analog converter 109 that also receives an input from the comb filter 102. A frequency analyzer 110 receives the output of the digital to analog converter 109 and supplies an input to the module sequence detector 112 and to the module digital interface address decode and data register 113. The output of the module digital interface address decoder and data receiver 113 is supplied to the display indicator driver 114 which drives the indicator 22.

The locator module 54 receives outputs from the collector microcomputer 52 and determines the location of a fault and indicates this on the indicator 22.

Figure 6A:
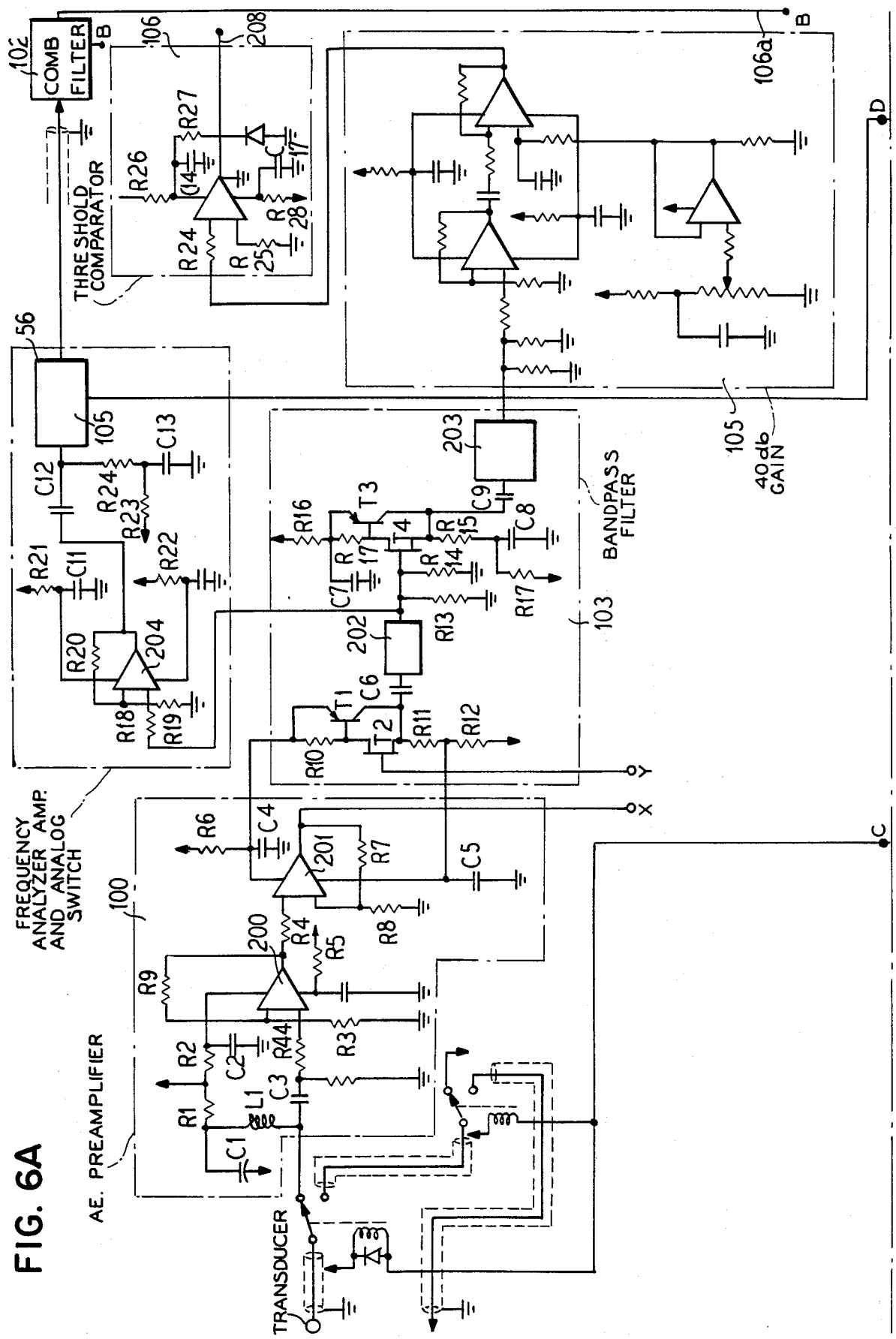

FIGS. 6A through 6H comprise electrical schematic diagrams of the block units illustrated in FIG. 5. For example, FIG. 6A illustrates the pre-amplifier 100 which comprises a plurality of resistors, capacitors and inductors and integrated circuits 200 and 201. The output of the pre-amplifier 100 is supplied to the band pass filter 103 which includes a 100 kHz high pass filter 202 as well as a 400 kHz low pass filter 203. The frequency analyzer 56 is connected to the output of the band pass 103 and includes operational circuit 204 and a switch 105. The output of the frequency analyzer amplifier 56 is supplied to the comb filter 102 which supplies an output to the digital to analog converter 109 illustrated in FIG. 6B through lead 106a. The band pass filter 103 also supplies an output to the 40 dB gain amplifier 105 which supplies an output to the threshold comparator 106. The threshold comparator 106 produces an output on lead 208 which is supplied to the ring down counter 107 illustrated in FIG. 6B.

Figure 6B:
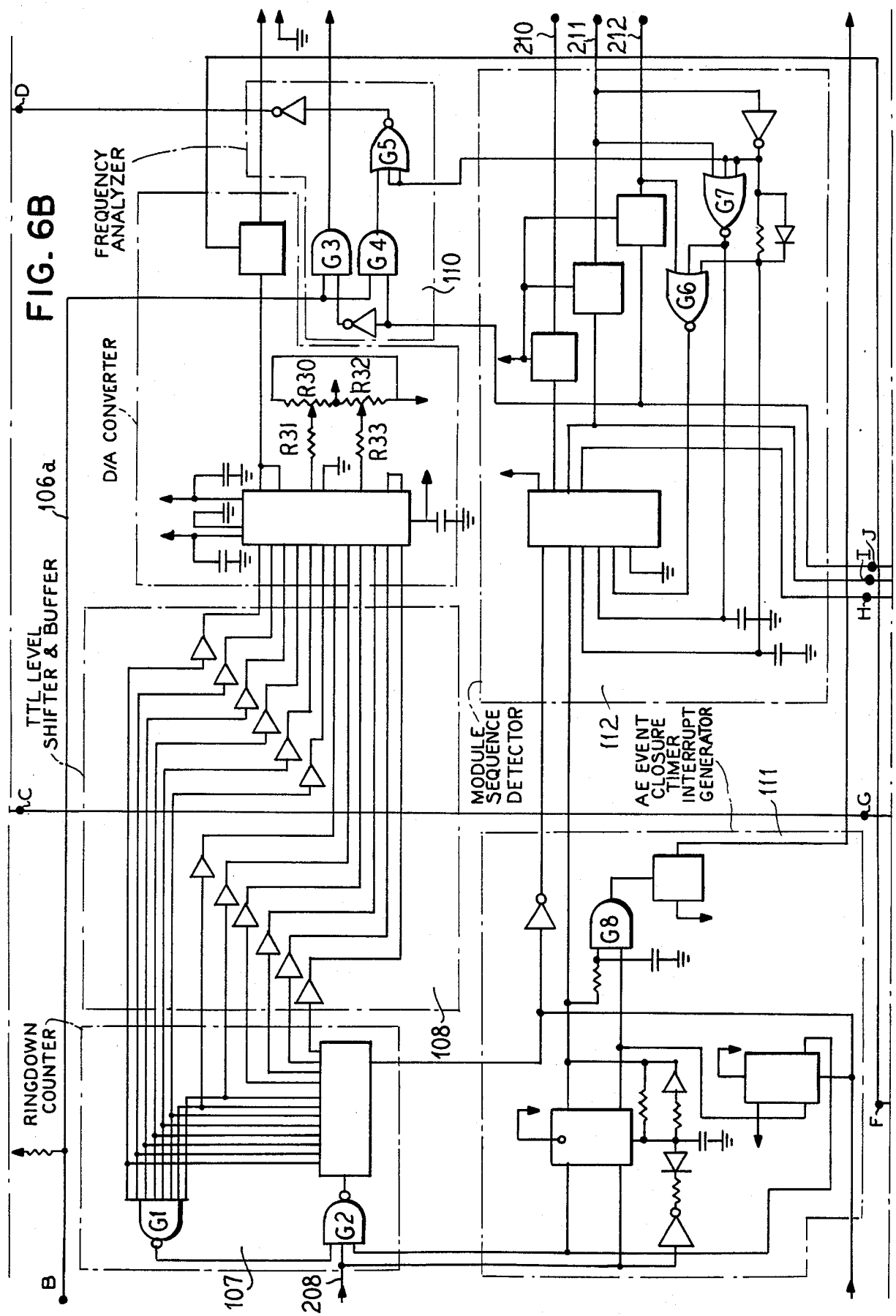
Figure 6C:
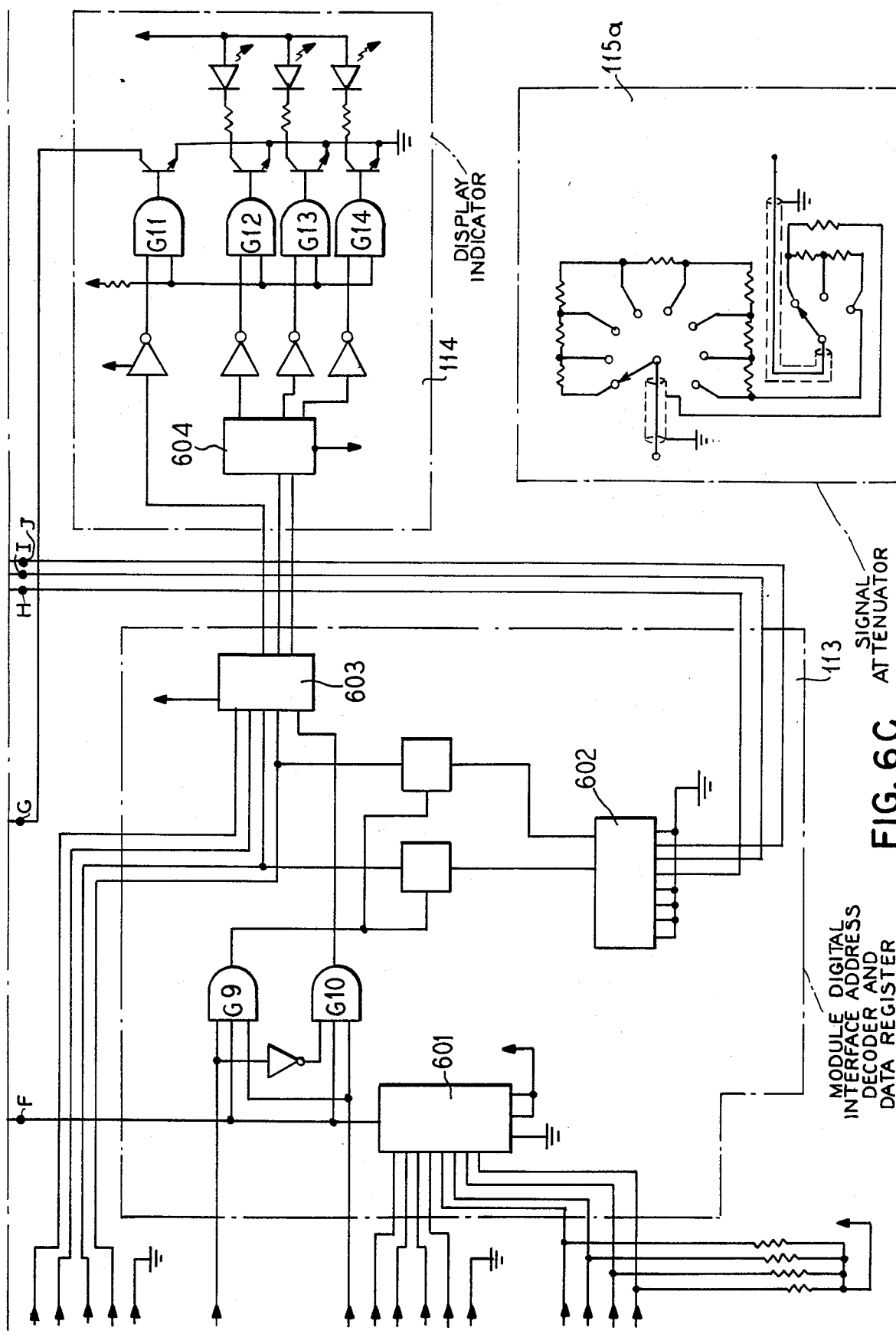

As shown in FIG. 6B and 6C, the output of the ring down counter 107 is supplied to the level shifter and buffer 108 which supplies an output to the digital to analog converter 109. The frequency analyzer 110 receives the output of the converter 109 and is connected to the module sequence detector 112 which is connected to the transducers through leads 210, 211 and 212 respectively. The AE event closure timer and interrupt generator 111 is also connected to the module sequence detector 112 as shown. The module digital interface address decoder and data register 113 is illustrated in FIG. 6C and is connected to the display indicator 114.

Figure 6D:
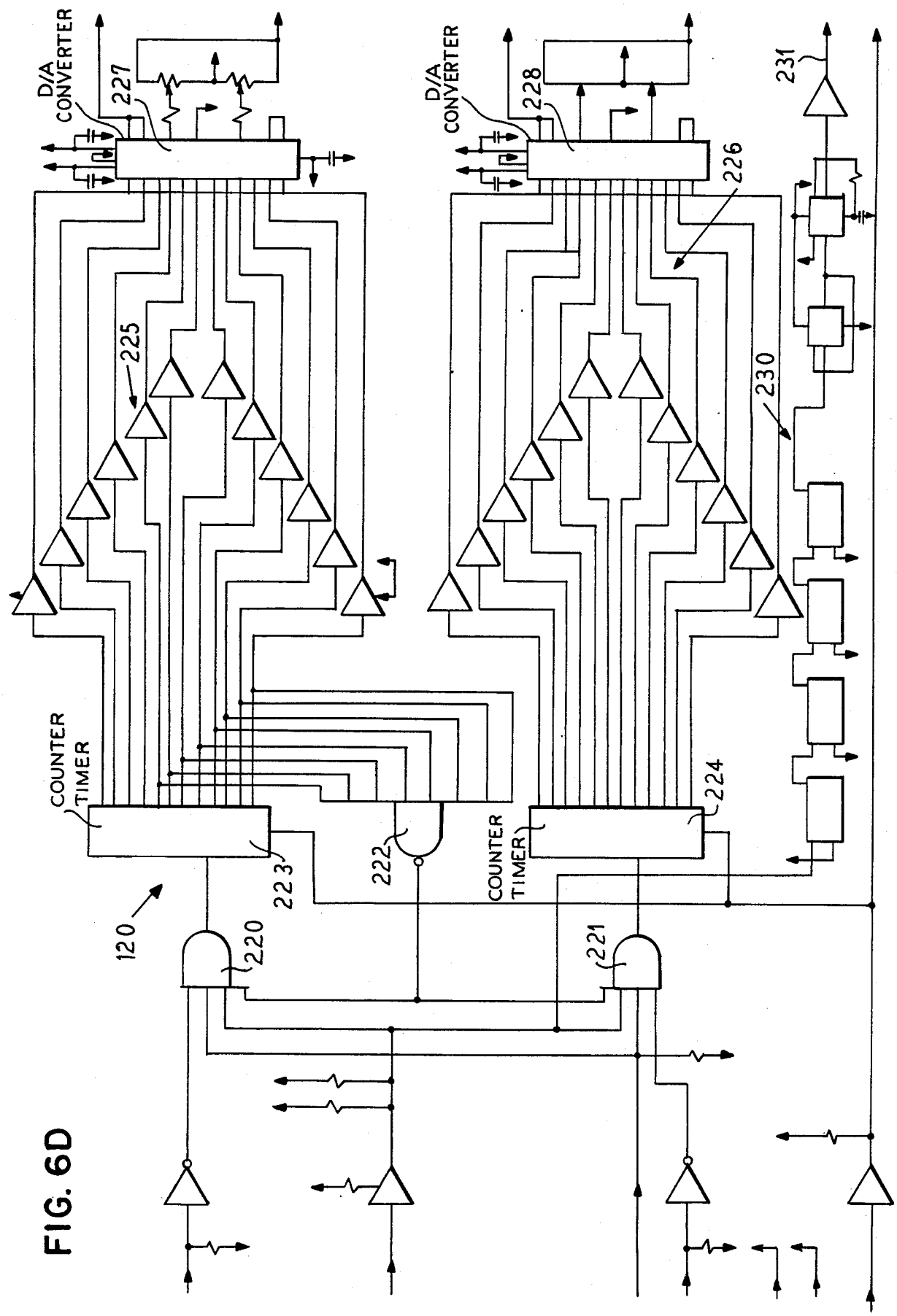

FIG. 6D illustrates the locator module 120 which includes gates 220 and 221 which receive inputs from the transducers 11, 12 and 13 and supply inputs to a first counter timer 223 and to a second counter timer 224. The output of the counter timer 223 is connected to a level signal buffer 225 and the output of the timer 224 is connected to a level signal buffer 226. A digital to analog converter 227 receives the output of the buffer 225 and a digital to analog converter 228 receives the output of the buffer 226. A clock frequency divider 230 produces a clock output signal on lead 231. FIG. 6E illustrates the AE frequency module 110 and includes a plurality of filters with center frequencies at different frequencies as, for example, the filter 240 is centered at 920 kHz. The filter 241 is centered at 675 kHz, the filter 242 is centered at 500 kHz, the filter 243 is centered at 370 kHz, the filter 244 is centered at 270 kHz, the filter 245 is centered at 200 kHz, the filter 246 is centered at 150 kHz and the filter 247 is centered at 110 kHz. The control signal is generated by the control module 248.

Figure 6F:
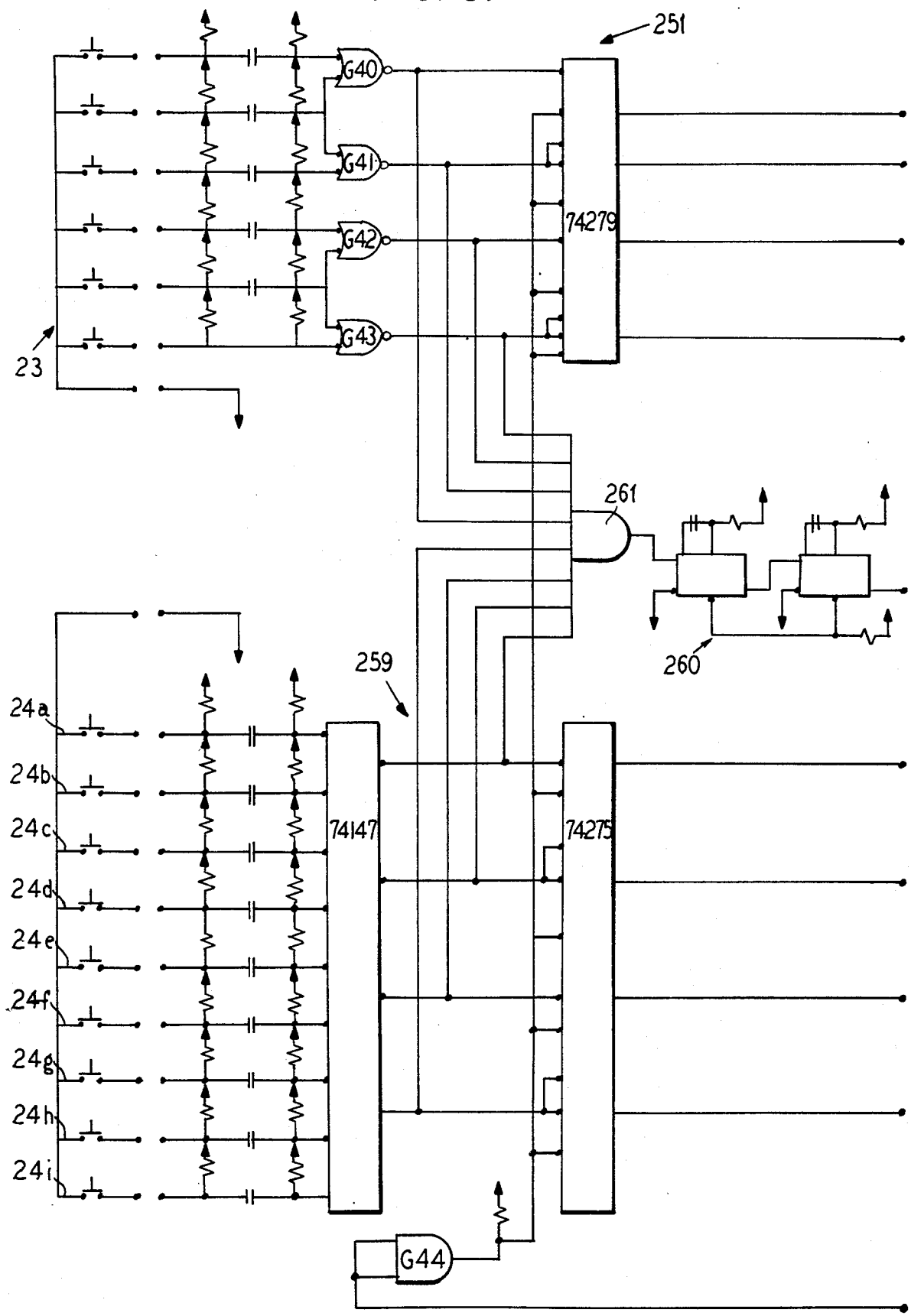
Figure 6G:
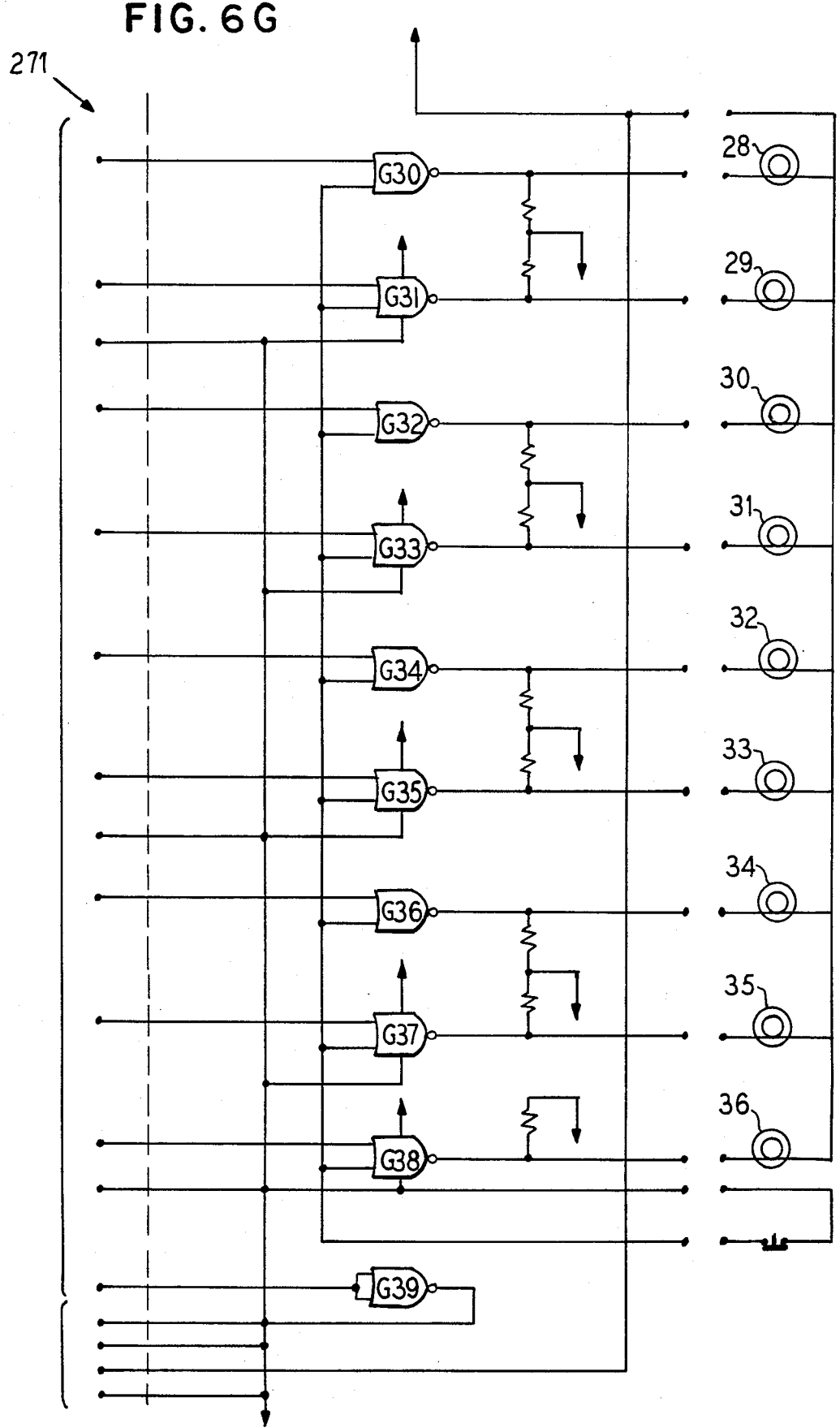

FIG. 6F illustrates the data encoder and storage latch 251 and shows the key pad switches 23. The front panel buttons 28 through 36 are illustrated and supply an input to a type 714147 integrated circuit which supplies an output to a type 74275 integrated circuit. An interrupt-delay and generator 269 is connected through a gate 261 to the front panel and push button circuits 259 and the switch pulse former 251. FIG. 6G illustrates the front panel lamp driver 271 which drives the indicator lamps 28 through 36.

FIG. 6H illustrates the address module 280, the digital data bus 281 and the calibrate pulse unit 282.

In operation the three transducers 11, 12, and 13 are mounted as illustrated in FIG. 1. Transducer 13 which is driven by a pulser which serves only to assure proper system operation by supplying a pulse which simulates an acoustic emission burst. The proper receipt of this pulse at transducers 11 and 12 as indicated by the LED Level Indicator on the analog modules 19, 20 and 21, assures the operator that the transducers, pre amps, and connecting cables, are all operational. Furthermore, the proper location of the pulsed transducer 13 by the locator module 54 and the corresponding indicator on the display terminal 22 insures proper location calibration of the AE monitoring system.

Acoustic mission bursts are generated by the bridge 10 as it is subjected to loading and received at transducers 11 and 12.

Only if these received bursts pass sequentially an energy (ring down count) test, and a rate test, as well as a locational tolerance test, are AE flaw indication generated on the display 22 at the location of the flaw activity. It is the three step energy, rate, location test that provides great immunity to random background AE noise and allows the system to effectively detect, locate, and characterize flaw growth in a complex structure operating with high background noise present.

The present invention deals with the noise problem which exists in this environment. As a bridge is loaded many normal factors and structures generate acoustic emission noise. For example, the bolts move as the beams flex which generates noise. 99.9% of the noise generated results from structural features which are o.k. and the problem solved with the present invention is to isolate the very small percent of acoustic emission noise which originates from flaws and cracks. I have discovered that acoustic emission from cracks occurs at a higher rate than acoustic emission from structures which are alright and I use this discovery to locate the flaws. All acoustic emission from a flaw comes from a local area.

Since there are many sources of acoustic energy, a rate test alone would not isolate the flaw.

By subjecting the received energy to an energy test which can be done by a count down generator and selecting a window which allows energy above a preset level and below a preset level to pass a selection of energy levels in which flaw activity will occur is selected.

Then the events which pass the energy test are subjected to a rate test and if it passes this test, also then is subjected to a location test to locate the fault.

In steel, 16 micro seconds transit time equals about one inch.

Although the tests have been in a sequence of (1) energy, (2) rate and (3) location, it is to be realized that the sequence can be varied to obtain the same results.

The present invention not only subjects each of the AE events to an amplitude discrimination, but also subjects them to a rate discrimination and only if the AE events pass both of these criteria are supplied to a locator discrimination which determines the position of the fault.

Although the invention has been described with respect to preferred embodiments, it is not to be so limited as changes and modifications can be made which are within the full intended scope of the invention as defined by the appended claims.

I claim as my invention:

1. Apparatus for detecting and locating flaws in metal bridges or other specimens subject to acoustical emission comprising, first, second and third acoustical transducers with means for attaching them to a bridge in a predetermined pattern with the transducers spaced generally in a straight line, a pulser connected to the one of said transducers which is mounted between the other two transducers, first and second amplifiers connected, respectively, to said first and second transducers, amplitude discriminating means connected to said first and second amplifiers to pass signals with amplitudes above a predetermined level, rate discrimination means connected to the output of said amplitude discriminating means to pass signals which have rates within predetermined criteria, location discriminating means receiving the outputs of said rate discriminating means to determine if the events which pass the energy and rate discrimination tests all come from the same location within preset tolerances, and locating flaws wherein said amplitude discriminating means and said rate discriminating means comprise a microcomputer, and wherein said location determining means is connected to said microcomputer.

2. Apparatus for detecting and locating flaws according to claim 1 including a frequency analyzer connected between said location determining means and said rate discrimination means.

3. Apparatus for detecting and locating flaws according to claim 1 wherein said output means comprises an oscilloscope.

4. Apparatus for detecting and locating flaws according to claim 1 wherein said output means comprises a printer.

5. Apparatus for detecting and locating flaws according to claim 1 wherein level setting means are provided on said amplitude discriminating means to set said predetermined level.

6. Apparatus for detecting and locating flaws according to claim 1 wherein rate setting means are provided on said rate determining means.

7. The method of detecting and locating flaws in metal bridges or other specimens comprising the steps of, receiving acoustical emission energy at two different locations on the specimen which form a straight line, periodically pulsing the middle one of the three locations, amplitude discriminating the acoustical emission received from said two locations to pass signals above a predetermined level, rate discriminating the acoustical emission which is above said preset level to pass events which exceed a predetermined rate, and determining with a microcomputer the location of flaws in said specimen from the events which exceed said predetermined rate, and including indicating the location of flaws in said specimen.

* * * * *